United States Patent [19]
Cooper et al.

[11] Patent Number: 4,788,205
[45] Date of Patent: Nov. 29, 1988

[54] DIHYDROPYRIDINE ANTI-ALLERGIC AND ANTIINFLAMMATORY AGENTS

[75] Inventors: Kelvin Cooper; Michael J. Parry, both of Deal; Peter E. Cross, Canterbury; Kenneth Richardson, Birchington, all of England

[73] Assignee: Pfizer Inc., New York, N.Y.

[21] Appl. No.: 75,379

[22] Filed: Jul. 20, 1987

[30] Foreign Application Priority Data

Aug. 29, 1986 [GB] United Kingdom ................. 8620880

[51] Int. Cl.$^4$ .................. C07D 401/12; A61K 31/415
[52] U.S. Cl. .................................... 514/333; 514/338; 514/341; 514/318; 514/252; 514/227.8; 546/278; 514/235.5; 546/270; 546/277; 546/256; 546/193; 544/131; 544/58.1; 544/365

[58] Field of Search ............... 546/318, 277, 270, 256, 546/193, 268; 514/356, 333, 341, 338, 318, 236, 222, 252; 544/131, 58.1, 365

[56] References Cited

U.S. PATENT DOCUMENTS

3,867,393 2/1975 Meyer et al. ..................... 546/321
4,515,799 5/1985 Campbell et al. .................. 546/271

FOREIGN PATENT DOCUMENTS

2228377 1/1974 Fed. Rep. of Germany .

*Primary Examiner*—Jane T. Fan
*Attorney, Agent, or Firm*—Peter C. Richardson; J. Trevor Lumb; James M. McManus

[57] ABSTRACT

Certain 4-aryl-5-carbamoyl-1,4-dihydropyridines useful in the treatment of allergic and inflammatory conditions in mammals.

11 Claims, No Drawings

DIHYDROPYRIDINE ANTI-ALLERGIC AND ANTIINFLAMMATORY AGENTS

BACKGROUND OF THE INVENTION

This invention relates to dihydropyridines, specifically to certain 4-aryl-5-carbamoyl-1,4-dihydropyridines which are useful in the treatment of allergic and inflammatory conditions in humans and animals.

A number of 1,4-dihydropyridines have been previously described as antiischaemic and antihypertensive agents. These compounds are able to inhibit the movement of calcium into cells and are thus active in the treatment or prevention of a variety of cardiac conditions or as antihypertensive agents. (See for example EP-A-No. 100189.) However the compounds of the present invention are potent and selective antagonists of platelet activating factor and as such they have clinical utility in a quite different area, namely for treating allergic and inflammatory conditions such as asthma and arthritis respectively.

Platelet activating factor (PAF) 1-O-alkyl-2-acetyl-sn-glyceryl-3-phosphorylcholine) is an ether phospholipid whose structure was first elucidated in 1979. It is produced by, released from and interacts with many pro-inflammatory cells, platelets and the kidney. In addition to potent platelet aggregating activity, PAF exhibits a wide spectrum of biological activities elicited either directly or via the release of other powerful mediators such as thromboxane $A_2$ or the leukotrienes. In vitro, PAF stimulates the movement and aggregation of neutrophils and the release therefrom of tissue-damaging enzymes and oxygen radicals. These activities contribute to actions of PAF in vivo consistent with it playing a significant role in inflammatory and allergic responses. Thus, intradermal PAF has been shown to induce an inflammatory response, with associated pain, accumulation of inflammatory cells and increased vascular permeability, comparable with the allergic skin reaction following exposure to allergen. Similarly, both the acute bronchoconstriction and chronic inflammatory reactions elicited by allergens in asthma can be mimicked by intratracheal administration of PAF. Accordingly agents which antagonise the actions of PAF and, consequently also prevent mediator release by PAF, will have clinical utility in the treatment of a variety of allergic, inflammatory and hypersecretory conditions such as asthma, arthritis, rhinitis, bronchitis and urticaria.

In addition to the above, PAF has been implicated as being involved in a number of other medical conditions. Thus in circulatory shock, which is characterised by systemic hypotension, pulmonary hypertension and increased lung vascular permeability, the symptoms can be mimicked by infusion of PAF. This coupled with evidence showing that circulating PAF leaves the increased by endotoxin infusion indicate that PAF is a prime mediator in certain forms of shock. Intravenous infusion of PAF at doses of 20–200 pmol $kg^{-1}$ $min^{-1}$ into rats results in the formation of extensive haemorrhagic erosions in the gastric mucosa and thus PAF is the most potent gastric ulcerogen yet described whose endogenous release may underlie or contribute to certain forms of gastric ulceration. Psoriasis is an inflammatory and proliferative disease characterised by skin lesions. PAF is pro-inflammatory and has been isolated from lesioned scale of psoriatic patients indicating PAF has a role in the disease of psoriasis. And finally, increasing evidence supports a potential pathophysiological role for PAF in cardiovascular disease. Thus recent studies in angina patients show PAF is released during atrial pacing. Intracoronary injection of PAF in pigs induces a prolonged decrease in coronary flow and in guinea pig hearts it induces regional shunting and ischaemia. Thus the compounds of the invention could be of value in the treatment of any of these conditions.

SUMMARY OF THE INVENTION

According to the present invention there are provided compounds of the formula:

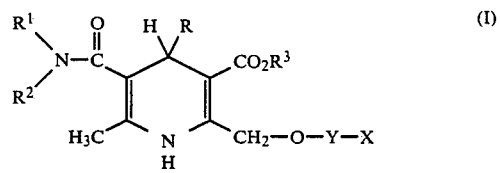

or a pharmaceutically acceptable salt thereof wherein R is phenyl, fluorophenyl, chlorophenyl, trifluoromethylphenyl, difluorophenyl, methylphenyl or methoxyphenyl; $R^1$ is hydrogen, alkyl of one to six carbon atoms, cycloalkyl of three to seven carbon atoms, cycloalkylmethyl of four to eight carbon atoms, phenyl, phenylalkyl of seven to nine carbon atoms, indanyl, thenyl, pyridyl, methylpyridyl, picolyl, chloropyridyl, 2-thiazolyl, methyl-2-thiazolyl, dimethyl-2-thiazolyl, 2-benzothiazolyl, 6-alkoxy-2-benzothiazolyl said alkoxy having one to three carbon atoms, 1,3,4-thiadiazol-2-yl, 5-methyl-1,3,4-thiadiazol-2-yl, quinolyl, 3-isoxazolyl, 5-methyl-3-isoxazolyl, methylpyrazol-1-ylmethyl, or alpha-carboalkoxybenzyl said alkoxy having one to three carbon atoms; $R^2$ is hydrogen or alkyl of one to six carbon atoms; $R^1$ and $R^2$ when taken together with the nitrogen to which they are attached are piperidine, morpholine, thiomorpholine, piperazine or N-substituted piperazine said substituent being alkyl of one to five carbon atoms, phenyl or alkanoyl of one to four carbon atoms; $R^3$ is alkyl of one to six carbon atoms or ethoxyalkyl of four to six carbon atoms; Y is alkylene of two to eight carbon atoms, having at least two carbon atoms in the chain linking X to the oxygen atom; and X is imidazol-1-yl optionally substituted with from one to three methyl and chloro groups.

A preferred group of compounds are those where R is 2-chlorophenyl, Y is —$(CH_2)_2$—, $R^3$ is ethyl and $R^2$ is hydrogen. Especially preferred within this group are compounds where X is 2,4,5-trimethylimidazol-1-yl and $R^1$ is t-butyl, 2-pyridyl, 6-methyl-2-pyridyl, 2-thiazolyl or 2-benzothiazolyl.

Also included in the instant invention is a method for treating an allergic or inflammatory condition in a mammal which comprises administering to said mammal an anti-allergic or antiinflammatory effective amount of the compounds of the present invention and a pharmaceutical composition comprising an anti-allergic or antiinflammatory effective amount of a compound of the present invention and a pharmaceutically acceptable carrier or diluent.

The compounds of the formula (I) contain at least one asymmetric centre and exist as one or more pairs of enantiomers. Such pairs of individual isomers may be separable by physical methods, e.g by fractional crystallisation or chromatography of the parent compounds or of a suitable salt or derivatives thereof. The invention includes all the enantiomers whether separated or not.

The pharmaceutically acceptable acid addition salts of the compounds of the formula (I) which form such salts are those formed from acids which form non-toxic acid addition salts, for example the hydrochloride, hydrobromide, sulphate or bisulphate, phosphate or acid phosphate, acetate, citrate, fumarate, gluconate, lactate, maleate, succinate and tartrate salts.

DETAILED DESCRIPTION OF THE INVENTION

The compounds of formula I may be obtained by a number of different processes in accordance with the invention:

(a) In one process the compounds are obtained by the Hantzsch synthesis, according to the following reaction scheme:

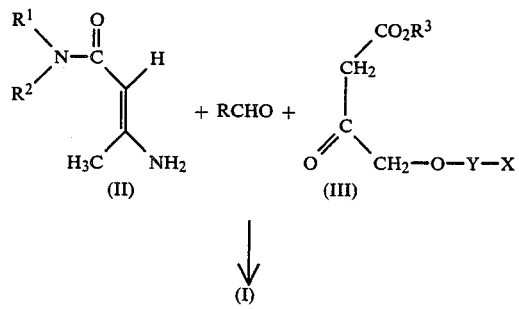

wherein R, $R^1$, $R^2$, $R^3$, Y and X are as previously defined.

In a typical procedure, the ketoester (III) and aldehyde are heated under reflux in a suitable organic solvent, e.g. a $C_1$–$C_4$ alkanol such as ethanol, for about 15 minutes, and then the amino-crotonamide (II) is added. Alternatively the aminocrotonamide (II), the ketoester (III) and the aldehyde can be heated together in the solvent. Preferably a small amount of a lower alkanoic acid such as acetic acid is added to neutralise the solution. The resulting solution can then be heated at 60°–130° C., preferably under reflux, until the reaction is essentially complete, typically in 24 hours or less. The product of the formula (I) can then be isolated and purified by conventional procedures, for example by partition, recrystallisation or by chromatography.

The ketoesters (III) are either known compounds or can be prepared by methods analogous to those of the prior art, such as the method described in European Pat. No. 100189 which is essentially the method of Troostwijk and Kellogg, J.C.S. Chem. Comm., 1977, page 932, or as described in the Preparations given hereafter. Similarly the amino-crotonamides (II) are either known compounds or can be prepared by conventional procedures, for example from the ketoamide by reaction with ammonia. Also the aldehydes RCHO are either known or can be prepared by known methods in accordance with literature precedents.

(b) In an alternative procedure, the compounds of formula (I) wherein X is 1-imidazolyl substituted by $C_1$–$C_4$ alkyl groups are prepared from an amine of the formula:

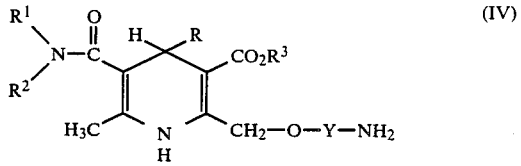

by reaction with a dione of the formula

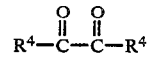

followed by addition of an aminal of formula $R^5CH(NH_2)_2$ wherein each $R^4$ and $R^5$ is $C_1$–$C_4$ alkyl, (in practice, these aminals exist as trimers.)

The reaction is typically performed by adding excess of the dione to a cooled solution of the amine (IV) in an organic solvent, for example methanol, and after one or two hours the aminal e.g. acetaldehyde ammonia trimer, is added. The reaction is generally complete within several hours and the product is then isolated and purified by conventional procedures e.g. by chromatography.

The starting amines of formula IV are prepared by conventional methods, for example by the Hantzsch synthesis described under (a) but using the compound of formula (III) wherein X is azido. The product is then reduced by catalytic hydrogenation to yield the amine (IV).

The activity of the compounds of the invention is shown by their ability to inhibit the platelet aggregating activity of PAF in vitro. Testing is performed as follows:

Blood samples are taken from either rabbit or man into 0.1 vol disodium ethylenediamine tetraacetic acid buffer and the samples centrifuged for 15 minutes to obtain platelet rich plasma. The plasma is further centrifuged to give a platelet pellet which is washed with a buffer solution (4 mM $KH_2PO_4$, 6 mM $Na_2HPO_4$, 100 mM NaCl, 0.1% glucose and 0.1% bovine serum albumin, pH 7.25) and finally resuspended in buffer solution to a concentration of $2 \times 10^8$ platelets/ml. A sample (0.5 ml) is pre-incubated with stirring for two minutes at 37° C. in a Paton aggregometer, either with vehicle alone, or with vehicle containing the particular compound under test. PAF is added at a sufficient concentration to give a maximum aggregating response in the absence of test compound ($10^{-8}$ to $10^{-9}$ molar), and the platelet aggregation is measured by following the increase in light transmission of the solution. The experiment is repeated in the presence of test compound at a range of concentrations and the concentration of compound required to reduce the response to 50% of its maximum value is recorded as the $IC_{50}$ value.

The activity of the compounds of formula (I) is also demonstrated in vivo by their ability to protect mice from the lethal effect of an injection of PAF. A mixture of PAF (50 μg/kg) and DL-propranolol (5 mg/kg), in 0.9% w/v sodium chloride is injected (0.2ml) via a tail vein into mice. The compounds under test are either injected into the tail vein immediately prior to the PAF/propanolol injection or administered orally by gavage two hours earlier. The compounds are tested at several doses in groups of 5 mice and the dose which reduces mortality to 50% is recorded as the $PD_{50}$ value.

The compounds are also tested for their ability to reduce PAF-induced bronchoconstriction in anaesthetised guinea pigs. In this test airways resistance and dynamic lung compliance are calculated from recordings of airflow and transpleural pressure and calculation of tidal volume. The bronchoconstriction induced by PAF (100 ng/kg) is determined. One hour after the initial dose of PAF the compound under test is administered and the PAF challenge repeated. The ability of the compound to reduce the bronchoconstrictor effect of PAF is calculated as a ratio.

For therapeutic use the compounds of the formula (I) will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcustaneously. For parenteral administration, they are best used in the form of a sterile aqueous solution which may contain other substances, for example, enough salts or glucose to make the solution isotonic with blood.

For administration to man in the curvative or prophylactic treatment of allergic bronchial conditions and arthritis, oral dosages of the compounds will generally be in the range of from 2-1000 mg daily for an average adult patient (70 kg). Thus for a typical adult patient, individual tablets or capsules contain from 1 to 500 mg of active compound, in a suitable pharmaceutically acceptable vehicle or carrier. Dosages for intravenous administration would typically be within the range 1 to 10 mg per single dose as required. For the treatment of allergic and bronchial hyper-reactive conditions, inhalation via a nebuliser or aerosol may be the preferred route of drug administration. Dose levels by this route would be within the range 0.1 to 50 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

Thus in a further aspect the invention provides a pharmaceutical composition comprising a compound of the formula (I), or a pharmaceutically acceptable salt thereof, together with a pharmaceutically acceptable diluent or carrier.

The invention also includes a compound of the formula (I), or a pharmaceutically acceptable salt thereof, for use in medicine, in particular in the treatment of allergic and inflammatory conditions in a human being.

The preparation of the compounds of the invention is further illustrated by the following Examples.

EXAMPLE 1

4-(2-Chlorophenyl)-3-methoxycarbonyl-6-methyl-5-(N-phenylcarbamoyl)-2-[2-(2,4,5-trimethylimidazol-1-yl)ethoxymethyl]-1,4-dihydropyridine N-Phenyl-3-ketobutanamide (0.35 g, 2.0 mmole) was dissolved in ethanolic ammonia (15 ml, 0.105M) and stirred overnight at room temperature. The solution was evaporated to yield N-phenyl-3-aminocrotonamide which was used directly. The crude residue was taken up in ethanol (30 ml) and 2-chlorobenzaldehyde (0.28 g, 2 mmole) and methyl 4-[2-(2,4,5-trimethylimidazol-1-yl)ethoxy]-3-ketobutanoate (0.53 g, 2 mmole) were added. The mixture was heated at reflux for 8 hours then cooled and the solution evaporated to dryness under reduced pressure. The residue was chromatographed on silica eluting with ethyl acetate containing an increasing proportion of up to 10% diethylamine. The fractions containing the product were combined and evaporated to yield the title compound (0.56 g, 51%). m.p. 135°-140° C. Found: C, 65.06; H, 6.14; N, 9.86. $C_{30}H_{33}ClN_4O_4 \cdot \frac{1}{2}H_2O$ requires C, 65.09; H, 6.10; N, 10.12%.

EXAMPLES 2-27

The following compounds were prepared by the method of Example 1 using as starting materials the appropriate N-substituted-3-ketobutanamide, 2-chlorobenzaldehyde and ethyl 4-[2-(2,4,5-trimethylimidazol-1-yl)ethoxy]-3-ketobutanoate:

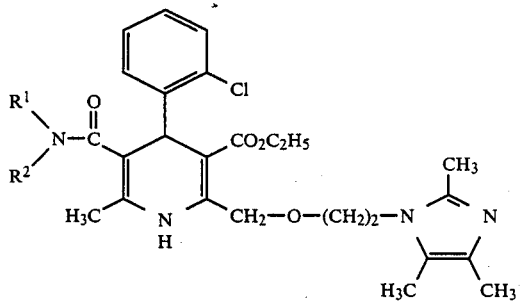

| Example No. | R¹ | R² | m.p. °C. | Analysis % (Theoretical in brackets) C | H | N |
|---|---|---|---|---|---|---|
| 2 | (cyclohexyl) | H | 137-144 | 65.85 (65.48) | 7.45 (7.26) | 9.72 (9.84) |

-continued

[Structure: dihydropyridine with 2-chlorophenyl, CO2C2H5, CONR1R2, CH3, and CH2-O-(CH2)2-N(trimethylpyrazine) substituents]

| # | R¹ | R² | m.p. (°C) | C | H | N |
|---|---|---|---|---|---|---|
| 3 | cyclopentyl-CH2- | H | 118–124 | 64.97 (64.90 | 7.56 7.49 | 9.62 9.46) |
| 4 | (CH₃)₃C— | H | 125–132 | 64.07 (64.13 | 7.19 7.24 | 10.05 10.32) |
| 5 | benzothiazol-2-yl | H | 225 (dec) | 61.73 (61.99 | 5.64 5.49 | 10.90 11.30) |
| 6 | pyridin-2-yl | H | ~160 | 63.78 (63.89 | 6.30 6.03 | 12.13 12.42) |
| 7 | 4-methylpyridin-2-yl | H | 90–95 | 63.52 (63.42 | 6.04 6.35 | 11.85 11.93) |
| 8 | 6-methylpyridin-2-yl | H | 110–115 | 64.18 (64.36 | 6.29 6.23 | 11.94 12.11) |
| 9 | 4-methylthiazol-2-yl | H | 170 (dec) | 58.89 (58.72 | 5.87 5.95 | 11.94 11.81) |
| 10 | 6-ethoxybenzothiazol-2-yl | H | 140–150 | 61.06 (61.46 | 5.85 5.77 | 10.32 10.54) |
| 11 | 4,5-dimethylthiazol-2-yl | H | 120–125 | 59.72 (59.34 | 6.15 6.10 | 11.42 11.62) |
| 12 | 3,5-dimethyl-1,2,4-thiadiazol-? | H | 176–183 | 57.18 (57.43 | 5.60 5.64 | 14.09 14.36) |
| 13 | pyridin-2-ylmethyl | H | ~217 | 64.26 (64.35 | 6.30 6.23 | 11.97 12.11) |
| 14 | C₂H₅— | C₂H₅ | gum | 62.03 (62.07 | 7.19 7.36 | 9.78 9.98) |

-continued
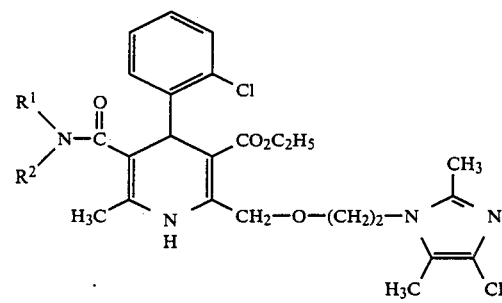
| | | | m.p. °C | C | H | N |
|---|---|---|---|---|---|---|
| 15 | 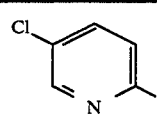 | H | 117–120 | 60.38 (60.20 | 5.46 5.56 | 11.35 11.70) |
| 16 | 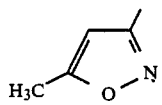 | H | 160 | 60.09 (59.89 | 6.15 6.15 | 11.60 12.04) |
| 17 | 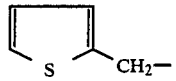 | H | 156–164 | 61.45 (61.79 | 6.04 6.05 | 9.44 9.61) |
| 18 | 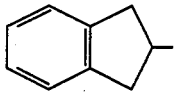 | H | 65–70 | 66.05 (65.74 | 6.78 6.65 | 9.38 9.02)[1] |
| 19 | 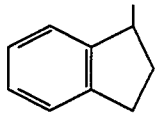 | H | 56–64 | 65.60 (65.74 | 6.92 6.65 | 9.74 9.02)[1] |
| 20 | 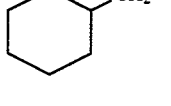 | H | 96–98 | 64.93 (64.90 | 7.74 7.49 | 9.06 9.46)[2] |
| 21 | 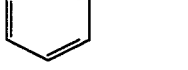 | H | Foam M.p. <30 | 65.24 (65.06 | 6.91 6.78 | 9.54 9.20)[1] |
| 22 | 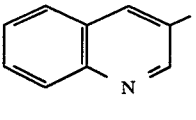 | H | 102–109 | 65.77 (65.95 | 5.94 6.06 | 10.68 10.88)[3] |
| 23 | 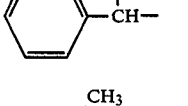 | H | 66–7 | 64.23 (64.75 | 6.68 6.37 | 8.80 8.63) |
| 24 | 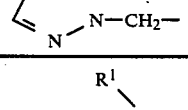 | H | 90–96 | 61.59 (62.01 | 6.36 6.42 | 14.00 14.46) |
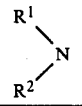
| Example No. | $R^1$ $R^2$ | | m.p. °C | Analysis % (Theoretical in brackets) | | |
|---|---|---|---|---|---|---|
| | | | | C | H | N |

-continued

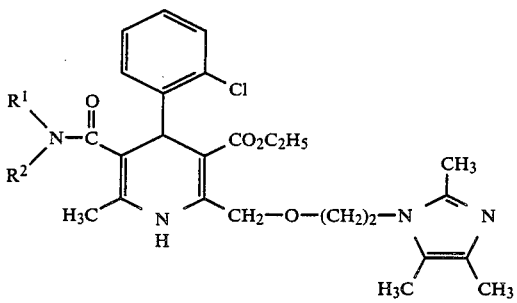

| | | | | | |
|---|---|---|---|---|---|
| 25 | N—(piperidine) | Foam m.p. <30 | 62.60 (62.87 | 7.16 7.21 | 9.71 9.77)[4] |
| 26 | CH₃CO—N⃝N— | 88–93 | 60.66 (61.06 | 6.91 6.76 | 10.68 11.00)[5] |
| 27 | (pyridyl)N⃝N— | 80–85 | 63.61 (63.19 | 6.55 6.55 | 12.41 12.51)[5] |

[1] Hydrate
[2] Hemihydrate
[3] Solvate with ½ ethyl acetate
[4] Hydrate
[5] Solvate with ½ ethyl acetate; hemihydrate

EXAMPLE 28

4-(2-Chlorophenyl)-3-isopropoxycarbonyl-5-(N-pyrid-2-ylcarbamoyl)-2-[2-(2,4,5-trimethylimidazol-1-yl)ethoxymethyl]-1,4-dihydropyridine The procedure of Example 1 was followed but using N-(pyrid-2-yl)-3-ketobutanamide (0.18 g), 2-chlorobenzaldehyde (0.15 g) and isopropyl 4-[2-(2,4,5-trimethylimidazol-1-yl)ethoxy]-3-ketobutanoate (0.3 g) as starting materials. The product was isolated as a white solid following chromatography on silica (0.105 g, 18%), m.p. 180°–182° C. Found: C, 64.25; H, 6.31; N, 12.08. C₃₁H₃₆ClN₅O₄ requires C, 64.42; H, 6.23; N, 12.12%.

EXAMPLES 29–32

The following compounds were prepared by the procedure of Example 28 using N-(6-methylpyrid-2-yl)-3-ketobutanamide, 2-chlorobenzaldehyde and the appropriate ketoester of formula (III).

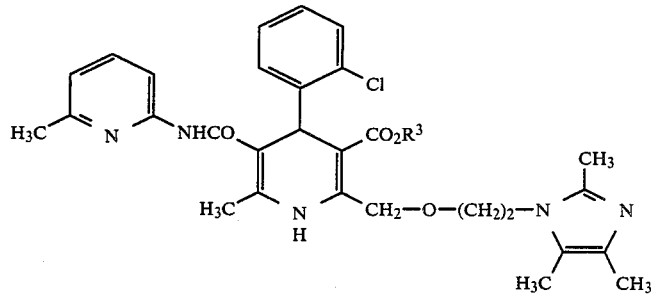

| Example No. | R³ | m.p. °C. | Analysis % (Theoretical in brackets) | | |
|---|---|---|---|---|---|
| | | | C | H | N |
| 29 | —C(CH₃)₃ | 90–93 | 65.69 (65.39 | 6.67 6.67 | 11.50 11.55) |
| 30 | —CH₂CH₂OCH₂CH₃ | gum | 61.36 (61.06 | 6.65 6.68 | 11.05 10.79)[1] |
| 31 | —(CH₂)₂CH₃ | 100–104 | 64.03 (63.94 | 6.17 6.54 | 11.68 11.65)[2] |
| 32 | —(CH₂)₄CH₃ | 83–87 | 64.39 | 6.63 | 11.27 |

-continued

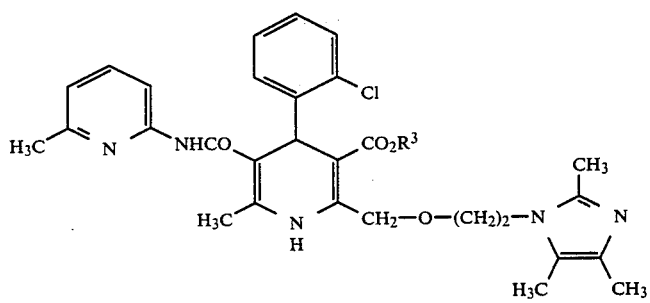

| Example No. | $R^3$ | m.p. °C. | Analysis % (Theoretical in brackets) | | |
|---|---|---|---|---|---|
| | | | C | H | N |
| | | | (64.43 | 6.72 | 11.38)[2] |

[1] 1.5 Hydrate
[2] Hemihydrate

EXAMPLES 33–40

The following compounds were prepared by the procedure of Example 1 using as starting materials the appropriate N-substituted-3-ketobutanamide, ethyl 4-[2-(2,4,5-trimethylimidazol-1-yl)ethoxy]-3-ketobutanoate and the appropriate substituted benzaldehyde derivative:

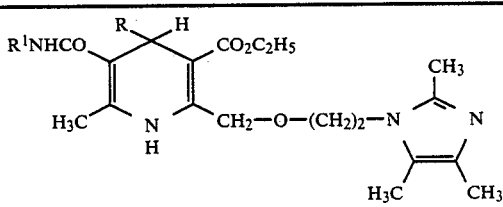

| Example No. | R | $R^1$ | m.p. °C. | Analysis % (Theoretical in brackets) | | |
|---|---|---|---|---|---|---|
| | | | | C | H | N |
| 33 | 3-Cl-phenyl | 2-pyridyl | 175–180 | 64.10 (63.88 | 6.32 6.08 | 12.12 12.42) |
| 34 | 2-F-phenyl | 2-pyridyl | 166–170 | 64.90 (64.73 | 6.19 6.34 | 12.56 12.58) |
| 35 | 2-CF₃-phenyl | 2-pyridyl | 185–190 | 62.28 (62.30 | 5.78 5.73 | 11.77 11.72) |
| 36 | 3-Cl-phenyl | 2-benzothiazolyl | 196 (dec) | 61.44 (61.53 | 5.71 5.57 | 11.46 11.21) |
| 37 | 2-F-phenyl | 2-benzothiazolyl | 213 (dec) | 63.42 (63.67 | 5.80 5.68 | 11.72 11.60) |

-continued

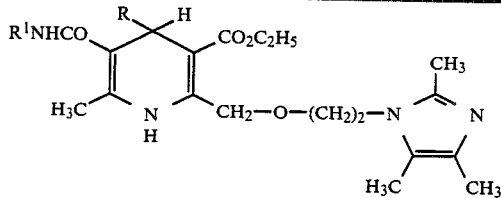

| Example No. | R | R¹ | m.p. °C. | Analysis % (Theoretical in brackets) | | |
|---|---|---|---|---|---|---|
| | | | | C | H | N |
| 38 | 2,4-difluorophenyl | 6-methyl-pyridin-2-yl | 191–195 | 63.93 (64.24 | 6.09 6.09 | 12,10 12.08) |
| 39 | 2-methoxyphenyl | 6-methyl-pyridin-2-yl | 170–176 | 66.42 (66.49 | 6.86 6.84 | 12.04 12.12)(1) |
| 40 | 2-methylphenyl | 6-methyl-pyridin-2-yl | 102–108 | 67.28 (67.30 | 7.48 7.10 | 11.97 12.26)(2) |

EXAMPLES 41–46

The following compounds were prepared by the procedure of Example 1 using as starting materials N-(2-thiazolyl)-3-keto-butanamide, 2-chlorobenzaldehyde and the appropriate ketoester of formula III.

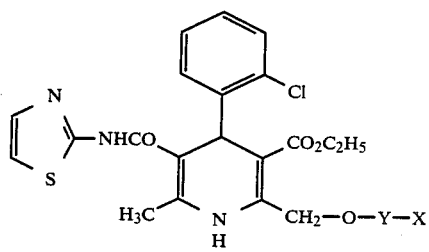

| Example No. | —Y—X | m.p. °C. | Analysis % (Theoretical in brackets) | | |
|---|---|---|---|---|---|
| | | | C | H | N |
| 41 | —CH₂—CH(CH₃)—CH₂—N(2-methylimidazol-1-yl) | 145–150 | 59.86 (59.00 | 6.23 5.62 | 12.4 12.29) |
| 42 | —CH₂—CH(CH₃)—N(2,4,5-trimethylimidazol-1-yl) | 188–189 | 57.56 (57.76 | 5.64 6.09 | 11.44 11.46) |
| 43 | —CH₂—C(CH₃)₂—N(2-methylimidazol-1-yl) | 167–170 | 58.82 (59.00 | 5.72 5.62 | 12.06 12.29) |

-continued

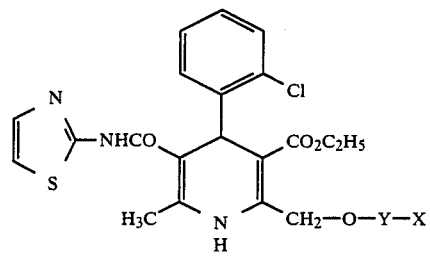

| Example No. | —Y—X | m.p. °C. | Analysis % (Theoretical in brackets) | | |
|---|---|---|---|---|---|
| | | | C | H | N |
| 44 | —CH₂—CH(CH₃)—N=C(CH₃)—N, H₃C, CH₃ (trimethylimidazole) | 151–163 | 62.49 (62.50 | 6.28 6.56 | 11.65 11.53) |
| 45 | —(CH₂)₂—N=C(CH₃)—N (tetrahydrobenzimidazole) | 143–144 | 63.99 (64.16 | 6.00 6.18 | 11.47 11.70) |
| 46 | —(CH₂)₂—N=C(CH₃)—N, Cl, Cl (dichloroimidazole) | 193–194 | 54.97 (54.76 | 4.49 4.72 | 11.33 11.41) |

EXAMPLE 47

4-(2-Chlorophenyl)-3-ethoxycarbonyl-5-[1-(4-methylpiperazinyl)carbonyl]-6-methyl-2-[2-(2,4,5-trimethylimidazol-1-yl)ethoxymethyl]-1,4-dihydropyridine 2,3-Butane dione (420 μl, 4.8 mmole) was added under nitrogen to a cooled solution at −10° C. of 2-(2-aminoethoxymethyl)-4-(2-chlorophenyl)-3-ethoxycarbonyl-5-[1-(4-methylpiperazinyl)carbonyl]-6-methyl-1,4-dihydropyridine (0.57 g, 1.2 mmole) in methanol (5 ml). The solution was stirred at −5±5° C. for 1½ hours and acetaldehyde ammonia trimer (0.65 g, 5.54 mmole) was then added at −10° C. and the mixture allowed to stand at 4° C. for 15 hours. Ammonium hydroxide (2 ml, 0.88) was then added to the solution which was subsequently diluted with ethyl acetate (50 ml), washed with water (50 ml) dried over magnesium sulphate and concentrated under reduced pressure. The residual oil was flash chromatographed on silica eluting with 5% diethylamine in ethyl acetate to give a gum which was triturated with n-pentane to yield the title product as a white solid (0.2 g, 30%). m.p. 80° C. Found: C, 62.53; H, 7.12; N, 11.92. $C_{30}H_{40}ClN_5O_4 \cdot \frac{1}{2}H_2O$ requires: C, 62.22; H, 7.14; N, 12.09%.

EXAMPLES 48–53

The following compounds were prepared by the method of Example 47 starting with the appropriate amine of formula IV.

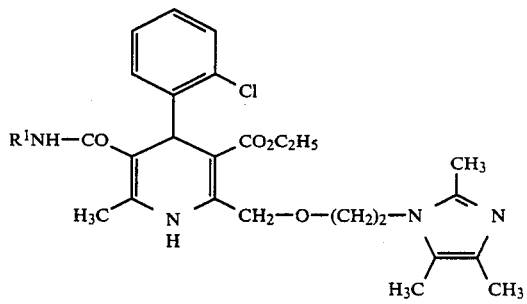

| Example No. | R¹ | m.p. °C. | Analysis % (Theoretical in brackets) | | |
|---|---|---|---|---|---|
| | | | C | H | N |
| 48 | phenyl | 176–180 | 64.49 (64.09 | 6.60 6.42 | 9.82 9.64) |
| 49 | H | gum | 55.20 (55.50 | 6.44 6.04 | 10.02 9.96) |
| 50 | (CH₃)₂CH— | gum | 62.21 (62.56 | 7.36 7.22 | 11.65 11.72) |

-continued

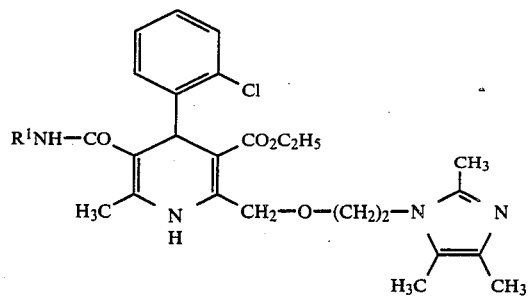

| Example No. | R¹ | m.p. °C. | Analysis % (Theoretical in brackets) | | |
|---|---|---|---|---|---|
| | | | C | H | N |
| 51 | ![benzyl]—CH₂— | gum | 65.57 (65.63 | 6.30 6.53 | 9.54 9.57) |
| 52 | CH₃ | 148–152 | 61.08 (61.23 | 6.99 6.72 | 10.89 10.98) |
| 53 | thiazolyl | ~147 | 57.79 (58.07 | 6.50 5.74 | 11.95 12.09) |

PREPARATION OF STARTING MATERIALS

1. Preparation of N-substituted-3-ketobutanamides

To a solution of 2-amino-4,5-dimethylthiazole (0.05 mole) in toluene (30 ml), cooled in ice was added diketene (0.05 mole) at such a rate that the temperature did not rise above 20° C. When addition was complete the mixture was stirred at room temperature for 2 hours and evaporated to dryness to give N-(4,5-dimethylthiazol-2-yl)-3-ketobutanamide (4.1 g), Rf (silica; diethylamine/ethyl acetate 1:19) 0.47; m.p. 191°–3° C.

Similarly made were:

N-(5-Methyl-1,3,4-thiadiazol-2-yl)-3-ketobutanamide, m.p. 178°–180° C., Rf (silica; diethylamine/ethyl acetate 1:19) 0.35.

N-(2-Pyridylmethyl)-3-ketobutanamide, (oil), Rf (silica; diethylamine/ethyl acetate 1:19) 0.39.

N-(4-Methylpiperazin-1-yl)-3-ketobutanamide, (oil), Rf (silica; diethylamine/ethyl acetate 1:19) 0.2.

In each case reaction with ethanolic ammonia is described in Example 1 gives the aminocrotonamide of formula II which was used directly to prepare the compounds of formula (I). Other N-substituted-3-ketobutanamide starting materials for Examples 2 to 27 were prepared in a similar manner from the appropriate amine.

2. Preparation of ketoesters (formula III)

1. Ethyl 4-[2-(2,4,5-trimethylimidazol-1-yl)ethoxy]-3-ketobutanoate

Sodium hydride (80% dispersion in oil) (7.8 g) was suspended in dry tetrahydrofuran (100 ml). 2-(2,4,5-Trimethylimidazol-1-yl)ethanol (20 g) was added and the suspension sonicated until there was no further gas evolution. Ethyl 4-chloroacetoacetate (21.3 g) in dry tetrahydrofuran (25 ml) was added over 0.75 hours with sonication, and sonication continued for a further 4 hours. The suspension was poured into 2N hydrochloric acid (200 ml) and the tetrahydrofuran removed under vacuum. The aqueous solution was washed with dichloromethane (3×50 ml) and then neutralised with potassium carbonate. The aqueous phase was extracted with dichloromethane (5×100 ml), the combined organic extracts dried over magnesium sulphate and solvent removed under vacuum. The crude product was chromatographed over silica eluting with a mixture of methanol and ethyl acetate (1:3) to yield the title compound as a pale red oil 13.5 g (37%).

2. Ethyl 4-[2-methyl-3-(2-methylimidazol-1-yl)propoxy]-3-ketobutanoate

Sodium hydride (80% dispersion in oil) (3.3 g) was washed with hexane, suspended in dry tetrahydrofuran (30 ml) and sonicated with 2-methylimidazole (8.2 g) until there was no further gas evolution. Ethyl-2-bromoisobutyrate (19.5 g) in dry tetrahydrofuran (10 ml) was added and the suspension sonicated for a further 4 hours. Methanol (1 ml) was added dropwise, the suspension filtered through solka flok and the solvents removed under vacuum. The crude product was dissolved in dichloromethane (150 ml), washed with brine (50 ml), dried over magnesium sulphate and the solvent removed under vacuum to yield ethyl 2-methyl-3-(2-methylimidazol-1-yl)propanoate as a foam (8.6 g, 44%). The product was taken up in tetrahydrofuran (40 ml) and added with stirring to a suspension of lithium aluminium hydride (1.6 g) in tetrahydrofuran (100 ml). The mixture was refluxed for 3 hours and cooled to 0° C. Water (5 ml) was added dropwise with vigorous stirring followed by 15% sodium hydroxide (2 ml) and a further quantity of water (10 ml). The slurry was filtered through solka flok, and the solvents removed under vacuum. The residue was dissolved in dichloromethane and washed with brine, the organic phase dried over magnesium sulphate and the solvent removed under vacuum to yield 2-methyl-3-(2-methylimidazol-1-yl)propanol as a foam (6.5 g, 97%). This product was reacted with ethyl 4-chloroacetoacetate (6.9 g) following the method described in 1 above to yield the title product as a red oil (1.5 g, 12%). NMR CDCl₃: δ 0.98 (d, J=6 Hz, 3H); 1.30 (t, J=6 Hz, 3H); 2.18 (m, 1H); 2.39 (s, 3H), 3.36 (m, 2H); 3.52 (s, 2H); 3.72 (d of d J=6 Hz, 9 Hz, 1H); 3.99 (d of d J=6 Hz, 9 hz, 1H); 4.14 (s, 2H); 4.20 (q, J=6 Hz, 2H); 6.82 (s, 1H); 6.92 (s, 1H).

3. Ethyl 4-[2-(2,4,5-trimethylimidazol-1-yl)propoxy]-3-ketobutanoate

A mixture of 2,4,5-trimethylimidazole (5.50 g), ethyl 2-bromo propanoate (9.05 g) and anhydrous potassium carbonate (8.0 g) in 100 ml of dry acetonitrile was heated under nitrogen at reflux with stirring for 48 hours. The mixture was filtered and the filter cake was washed with dichloromethane. The filtrate was concentrated under reduced pressure, the residue dissolved in 250 ml water and extracted with diethyl ether (3×150 ml). The extracts were dried over magnesium sulphate and concentrated under reduced pressure to give ethyl 2-(2,4,5-trimethylimidazol-1-yl)propanoate as a brown oil (4.03 g, 38%). This was dissolved in tetrahydrofuran (20 ml) and reduced with lithium aluminium hydride as previously described above to yield 2-(2,4,5-trimethylimidazol-1-yl)propanol (2.1 g, 66%) as a pale yellow solid. Reaction with ethyl 4-chloroacetate following the procedure described in 1 above yields the title product as a red oil (1.82 g, 54%). NMR, CDCl₃: δ 1.28 (t, J=6 Hz, 3H); 1.49 (d, J=6 Hz, 3H); 2.10 (s, 3H); 2.16 (s, 3H); 2.40 (s, 3H); 3.40 (s, 2H); 3.72 (m, 2H); 4.09 (s, 2H); 4.17 (q, J=6 Hz, 2H); 4.40 (m, 1H).

4. Ethyl 4-[2-(2-methylimidazol-1-yl)-2-methylpropoxy]-3-ketobutanoate

This compound was prepared following the procedure of 3 above using 2-methylimidazole and ethyl 2-bromo-isobutyrate. The title compound was obtained as a red oil. NMR, CDCl₃: δ 1.28 (t, J=6 Hz, 3H); 1.65 (s, 6H); 2.57 (s, 3H); 3.42 (s, 2H); 3.68 (s, 2H); 4.08 (s, 2H); 4.18 (q, J=6 Hz, 2H); 6.86 (s, 1H); 7.02 (s, 1H).

5. Ethyl 4-[2-(2-methyl-4,5,6,7-tetrahydrobenzimidazol-1-yl)ethoxy]-3-ketobutanoate This compound was prepared from 2-methyl-4,5,6,7-tetrahydrobenzimidazole by reaction with ethylbromoacetate followed by reduction with lithium aluminium hydride to give 2-(2-methyl-4,5,6,7-tetrahydrobenzimidazol-1-yl)ethanol. Reaction with ethyl 4-chloroacetoacetate following the procedure of 1 above gave the title compound as a red oil. NMR, CDCl₃: δ 1.26 (t, J=6 Hz, 3H); 1.80 (m, 4H); 2.40 (s, 3H); 2.49 (m, 2H); 2.57 (m, 2H); 3.44 (s, 2H); 3.67 (t, J=5 Hz, 2H); 3.92 (t, J=5 Hz, 2H); 4.13 (s, 2H); 4.20 (q, J=6 Hz, 2H).

6. Ethyl-4-[2-(4,5-dichloro-2-methyl-imidazol-1-yl)ethoxy]-3-ketobutanoate

The compound was prepared starting from 4,5-dichloro-2-methyl-imidazole following the procedure of 5 above. The product was a red oil. NMR, CDCl₃: δ 1.23 (t, J=6 Hz, 3H); 2.38 (s, 3H); 3.40 (s, 2H); 3.71 (t, J=4 Hz, 2H); 4.07 (t, J=4 Hz, 2H); 4.13 (s, 2H); 4.15 (q, J=6 Hz, 2H).

3. Preparation of amines (formula IV)

1. 2-(2-Aminoethoxymethyl)-4-(2-chlorophenyl)-3-ethoxycarbonyl-5-(4-methylpiperazinylcarbonyl)-6-methyl-1,4-dihydropyridine (a) N-(4-Methylpiperazinyl)-acetoacetamide (1.84 g), and ethanolic ammonia (20 ml) were stirred at room temperature under nitrogen for 48 hours. The solvent was evaporated and the resulting N-(4-methylpiperazinyl)-3-ketobutanamide, 2-chlorobenzaldehyde (1.41 g) and ethyl 4-(2-azidoethoxy)-3-ketobutanoate (2.15 g) in ethanol were heated at reflux for 8 hours. The solution was cooled, the solvent removed under reduced pressure and the residue chromatographed on silica eluting with a mixture of ethylacetate, methanol and concentrated ammonium hydroxide (95:5:0.5). Product containing fractions were combined, concentrated under reduced pressure and triturated with diethyl ether to give the 2-(2-azidoethoxymethyl)-1,4-dihydropyridine (0.9 g, 20%).

(b) The azide product from (a) (0.645 g) was dissolved in ethanol and hydrogenated at room temperature and 1.1 bar over 5% palladium on calcium carbonate for 4 hours. The solution was filtered, the filtrate concentrated under reduced pressure and the residue chromatographed on silica eluting with a mixture of ethyl acetate, methanol and concentrated ammonium hydroxide (90:10:1) to give the title compound as a white solid (0.6 g, 98%).

2. 2-(2-Aminoethoxymethyl)-4-(2-chlorophenyl)-3-ethoxycarbonyl-5-(N-isopropylcarbamoyl)-6-methyl-1,4-dihydropyridine (a) 2-Cyanoethyl acetoacetate (0.16 g) was stirred in ethanolic ammonia for 3 hours and evaporated to dryness. The product, 2-chlorobenzaldehyde (0.16 g) and ethyl 4-(2-azidoethoxy)-3-ketopropanoate (0.22 g) were heated at reflux in ethanol for 8 hours. The mixture was cooled, the solvent evaporated and the residue chromatographed on silica eluting with a mixture of diethyl ether and hexane to give 2-(2-azidoethoxy)-4-(2-chlorophenyl)-5-(2-cyanoethoxycarbonyl)-3-ethoxycarbonyl-6-methyl-1,4-dihydropyridine (9.6 g).

(b) Sodium hydroxide (0.24 g) in water (3 ml) was added to a solution of the above product in dioxan (15 ml) and the solution was stirred at room temperature for 3 hours and evaporated. The residue was partitioned between water and ethyl acetate, the aqueous layer separated, acidified to pH3 with hydrochloric acid and extracted with ethyl acetate. The extracts were dried over magnesium sulphate and evaporated to yield the 5-carboxylic acid (1.12 g). This was dissolved in dry dichloromethane (2 ml) and oxalyl chloride (90 microlitres) and N,N-dimethylformamide (1 drop) added. The mixture was stirred at room temperature for one hour and evaporated to dryness to yield the acid chloride. This was taken up in dichloromethane (1 ml) and added to a stirred solution of isopropylamine (0.15 g) in dry dichloromethane (5 ml) at −10° C. The mixture was allowed to warm to room temperature over 2 hours and the solution was then washed with 1M hydrochloric acid, dried over magnesium sulphate and the solvent evaporated. The residue was chromatographed on silica eluting with ethyl acetate containing a gradient of from 75% decreasing to 50% hexane to give 2-(2-azidoethoxymethyl)-4-(2-chlorophenyl)-3-ethoxycarbonyl-5-(N-isopropylcarbamoyl)-6-methyl-1,4-dihydropyridine (0.27 g).

(c) The product from (b) above was catalytically reduced over palladium on calcium carbonate to yield the title 2-(2-aminoethoxymethyl) product (0.11 g).

The starting amines of formula IV for Examples 47 to 53 were made in a similar manner using the appropriate amine in step (b).

We claim:

1. A compound of the formula

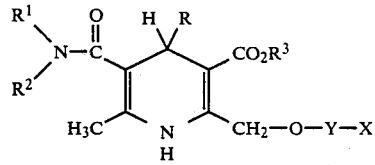

or a pharmaceutically acceptable salt thereof, wherein R is phenyl, fluorophenyl, chlorophenyl, trifluoromethylphenyl, difluorophenyl, methylphenyl or methoxyphenyl; $R^1$ is hydrogen, alkyl having one to six carbon atoms, cycloalkyl having from three to seven carbon atoms, cycloalkylmethyl having four to eight carbon atoms, phenyl, phenylalkyl having seven to nine carbon atoms, indanyl, thenyl, pyridyl, methylpyridyl, picolyl, chloropyridyl, 2-thiazolyl, methyl-2-thiazolyl, dimethyl-2-thiazolyl, 2-benzothiazolyl, 6-alkoxy-2-benzothiazolyl said alkoxy having one to three carbon atoms, 1,3,4-thiadiazol-2-yl, 5-methyl-1,3,4-thiadiazol-2-yl, quinolyl, 3-isoxazolyl, 5-methyl-3-isoxazolyl, methylpyrazol-1-ylmethyl, or alpha-carboalkoxybenzyl said alkoxy having from one to three carbon atoms; $R^2$ is hydrogen or alkyl having one to six carbon atoms; $R^1$ and $R^2$ taken together with the nitrogen to which they are attached form a heterocyclic ring selected from piperidine, morpholine, thiomorpholine, piperazine or N-substituted piperazine where said substituent is alkyl having one to five carbon atoms, phenyl or alkanoyl having one to four carbon atoms; $R^3$ is alkyl having one to six carbon atoms or ethoxyalkyl having four to six carbon atoms; Y is alkylene having two to eight carbon atoms, having at least two carbon atoms in the chain linking X to the oxygen atom; and X is imidazol-1-yl optionally substituted with from one to three substituents selected from methyl and chloro.

2. A compound of claim 1, wherein R is 2-chlorophenyl, Y is —$(CH_2)_2$, $R^3$ is ethyl and $R^2$ is hydrogen.

3. The compound of claim 2, wherein X is 2,4,5,-trimethylimidazol-1-yl and $R^1$ is t-butyl.

4. The compound of claim 2, wherein X is 2,4,5,-timethylimidazol-1-yl and $R^1$ is 2-pyridyl.

5. The compound of claim 2, wherein X is 2,4,5,-trimethylimidazol-1-yl and $R^1$ is 6-methyl-2-pyridyl.

6. The compound of claim 2, wherein X is 2,4,5-trimethylimidazol-1-yl and $R^1$ is 2-thiazolyl.

7. The compound of claim 2, wherein X is 2,4,5-trimethylimidazol-1-yl and $R^1$ is 2-benzothiazolyl.

8. A method of treating an allergic condition in a mammal which comprises administering to said mammal an anti-allergic effective amount of a compound according to claim 1.

9. A method of treating an inflammatory condition in a mammal which comprises administering to said mammal an antiinflammatory effective amount of a compound according to claim 1.

10. A pharmaceutical composition comprising an anti-allergic effective amount of a compound according to claim 1 and a pharmaceutically acceptable carrier or diluent.

11. A pharmaceutical composition comprising an antiinflammatory effective amount of a compound according to claim 1 and a pharmaceutically acceptable carrier or diluent.

* * * * *